United States Patent
Hübner et al.

(10) Patent No.: US 10,100,103 B2
(45) Date of Patent: Oct. 16, 2018

(54) OPSONIC AND PROTECTIVE MONOCLONAL ANTIBODIES AGAINST GRAM-POSITIVE PATHOGENS

(71) Applicant: Albert-Ludwigs-Universität Freiburg, Freiburg (DE)

(72) Inventors: Johannes Hübner, Freiburg (DE); Friederike Rossmann, Freiburg (DE); Andrea Kropec Hübner, Freiburg (DE)

(73) Assignee: ALBERT-LUDWIGS-UNIVERSITÄT FREIBURG, Freiburg (DE)

( * ) Notice: Subject to any disclaimer, the term of this patent is extended or adjusted under 35 U.S.C. 154(b) by 0 days.

(21) Appl. No.: 15/108,398

(22) PCT Filed: Nov. 17, 2014

(86) PCT No.: PCT/EP2014/074797
§ 371 (c)(1),
(2) Date: Jun. 27, 2016

(87) PCT Pub. No.: WO2015/101438
PCT Pub. Date: Jul. 9, 2015

(65) Prior Publication Data
US 2016/0318997 A1 Nov. 3, 2016

(30) Foreign Application Priority Data
Dec. 30, 2013 (EP) .................................... 13199849

(51) Int. Cl.
*A61K 39/00* (2006.01)
*C07K 16/12* (2006.01)
*G01N 33/569* (2006.01)

(52) U.S. Cl.
CPC ...... *C07K 16/1271* (2013.01); *C07K 16/1267* (2013.01); *G01N 33/56911* (2013.01); *A61K 2039/505* (2013.01); *C07K 2317/21* (2013.01); *C07K 2317/24* (2013.01); *C07K 2317/33* (2013.01); *C07K 2317/51* (2013.01); *C07K 2317/515* (2013.01); *C07K 2317/54* (2013.01); *C07K 2317/55* (2013.01); *C07K 2317/56* (2013.01); *C07K 2317/622* (2013.01); *C07K 2317/76* (2013.01); *G01N 2469/10* (2013.01)

(58) Field of Classification Search
None
See application file for complete search history.

(56) References Cited

U.S. PATENT DOCUMENTS 7,230,087 B2  6/2007  Pier et al.

FOREIGN PATENT DOCUMENTS

| EP | 2 476 702 A1 | 7/2012 |
|---|---|---|
| WO | WO 2005103084 A2 | 11/2005 |
| WO | WO 2007141278 A2 | 12/2007 |

OTHER PUBLICATIONS

Skolnick et al. (Trends in Biotechnology 18: 34-39, 2000).*
Greenspan et al. (Nature Biotechnology 7: 936-937, 1999).*
Ellis (Vaccines, W.B. Saunders Company, Chapter 29, 1988, pp. 568-574).*
Boslego et al (Vaccines and Immunotherapy, 1991, Chapter 17).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS 2012, vol. 109 No. 31, pp. 12272-12273).*
Theilacker, Christian, et al., "Protection Against *Staphylococcus aureus* by Antibody to the Polyglycerophosphate Backbone of Heterologous Lipoteichoic Acid," *The Journal of Infectious Diseases*, Apr. 1, 2012, 205: 1076-1085.

* cited by examiner

*Primary Examiner* — Robert A Zeman
(74) *Attorney, Agent, or Firm* — Saliwanchik, Lloyd & Eisenschenk

(57) ABSTRACT

The present invention in the fields of immunology and infectious diseases relates to opsonic and protective antibodies that are specific for Gram-positive bacteria, particularly to carbohydrate structures exposed on the surface of the bacteria. The invention includes monoclonal and chimeric antibodies, as well as fragments, regions and derivatives thereof. This invention also relates to the epitope to which the antibodies of the invention bind as well as the sequences, fragments, and regions of the epitopes. Both the antibodies and peptides that encompass the epitope, and regions and fragments thereof, may be used for diagnostic, prophylactic and therapeutic applications.

Figure 1:
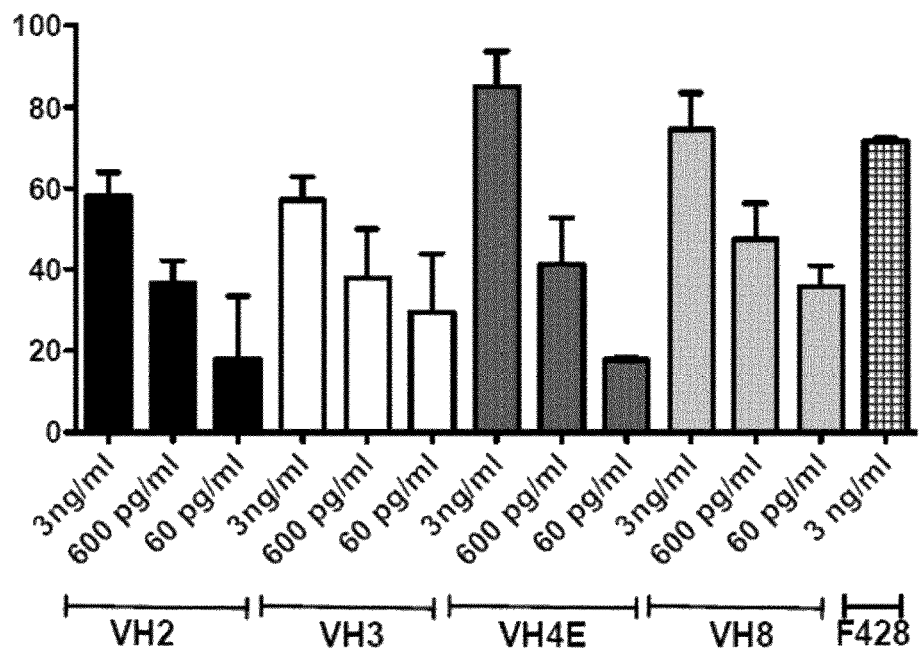

6 Claims, 7 Drawing Sheets
Specification includes a Sequence Listing.

SEQUENCE LISTING

<160> NUMBER OF SEQ ID NOS: 10

<210> SEQ ID NO 1
<211> LENGTH: 129
<212> TYPE: PRT

<213> ORGANISM: Homo sapiens

<400> SEQUENCE: 1

| | | | | | | | | | | | | | | |
|---|---|---|---|---|---|---|---|---|---|---|---|---|---|---|
| Leu | Thr | Met | Ala | Gly | Phe | Pro | Leu | Leu | Leu | Thr | Leu | Leu | Ile | His | Cys |
| 1 | | | | 5 | | | | | 10 | | | | | 15 | |
| Thr | Gly | Ser | Trp | Ala | Gln | Ser | Val | Leu | Thr | Gln | Pro | Pro | Ser | Val | Ser |
| | | | 20 | | | | | 25 | | | | | 30 | | |
| Ala | Ala | Pro | Gly | Gln | Arg | Val | Thr | Ile | Ser | Cys | Ser | Gly | Ser | Ser | Ser |
| | | 35 | | | | | 40 | | | | | 45 | | | |
| Asn | Leu | Gly | Asn | Asn | Phe | Ala | Ser | Trp | Tyr | Gln | Gln | Leu | Pro | Gly | Ala |
| | 50 | | | | | 55 | | | | | 60 | | | | |
| Ala | Pro | Arg | Leu | Leu | Ile | Tyr | Asp | Asn | Asp | Lys | Arg | Pro | Ser | Gly | Ile |
| 65 | | | | | 70 | | | | | 75 | | | | | 80 |
| Pro | Asp | Arg | Phe | Ser | Gly | Ser | Lys | Ser | Gly | Thr | Ser | Ala | Thr | Leu | Gly |
| | | | | 85 | | | | | 90 | | | | | 95 | |
| Ile | Thr | Gly | Leu | Gln | Thr | Gly | Asp | Glu | Ala | Asp | Tyr | Tyr | Cys | Gly | Thr |
| | | | 100 | | | | | 105 | | | | | 110 | | |
| Trp | Asp | Ser | Ser | Leu | Thr | Ala | Tyr | Val | Phe | Gly | Ser | Gly | Thr | Lys | Val |
| | | | 115 | | | | | 120 | | | | | 125 | | |
| Thr | | | | | | | | | | | | | | | |

<210> SEQ ID NO 2
<211> LENGTH: 389
<212> TYPE: DNA
<213> ORGANISM: Homo sapiens

<400> SEQUENCE: 2

```
ctcaccatgg ccggcttccc tctcctcctc acccttctca ttcactgcac agggtcctgg      60
gcccagtctg tgttgacgca gccgccctca gtgtctgcgg ccccaggaca gagggtcacc     120
atctcctgct ctggaagcag ctccaacctt gggaacaatt ttgcatcctg gtaccagcaa     180
ctcccaggag cagccccccg ctcctcatt tatgacaatg ataagcgacc ctcagggatt      240
cctgaccgat tctctggctc caagtctggc acgtcagcca ccctgggcat caccgggctc     300
cagactgggg acgaggccga ttattactgc ggaacatggg atagcagcct gactgcttat     360
gtcttcggaa gtgggaccaa ggtcaccgt                                       389
```

<210> SEQ ID NO 3
<211> LENGTH: 118
<212> TYPE: PRT
<213> ORGANISM: Homo sapiens

<400> SEQUENCE: 3

| | | | | | | | | | | | | | | |
|---|---|---|---|---|---|---|---|---|---|---|---|---|---|---|---|
| Gly | Val | Gly | Ala | Glu | Leu | Lys | Lys | Pro | Gly | Ala | Ser | Val | Lys | Val | Ser |
| 1 | | | | 5 | | | | | 10 | | | | | 15 | |
| Cys | Lys | Ala | Ser | Glu | Tyr | Thr | Phe | Thr | Thr | Tyr | Asp | Ile | Ile | Trp | Val |
| | | | 20 | | | | | 25 | | | | | 30 | | |
| Arg | Gln | Ala | Thr | Gly | Gln | Gly | Leu | Glu | Trp | Met | Gly | Trp | Met | Asn | Pro |
| | | | 35 | | | | | 40 | | | | | 45 | | |
| Asn | Ser | Gly | Asp | Thr | Gly | Phe | Ala | Gln | Lys | Phe | Gln | Asp | Arg | Val | Thr |
| | 50 | | | | | 55 | | | | | 60 | | | | |
| Leu | Thr | Arg | Asn | Thr | Ser | Ile | Ser | Thr | Ala | Tyr | Met | Glu | Leu | Ser | Ser |
| 65 | | | | | 70 | | | | | 75 | | | | | 80 |
| Leu | Arg | Ser | Glu | Asp | Thr | Ala | Val | Tyr | Tyr | Cys | Ser | Arg | Ala | Pro | Arg |
| | | | | 85 | | | | | 90 | | | | | 95 | |
| Tyr | Asp | Ser | Trp | Ser | Gly | Tyr | Tyr | Ser | Asp | Phe | Trp | Gly | Gln | Gly | Thr |

Leu Val Thr Val Ser Ser
        115

<210> SEQ ID NO 4
<211> LENGTH: 356
<212> TYPE: DNA
<213> ORGANISM: Homo sapiens

<400> SEQUENCE: 4
atggagttgg ggctgagctg aagaagcctg gggcctcagt gaaggtctcc tgcaaggctt    60
ccgaatacac cttcaccact tatgatatca tctgggtgcg gcaggccact ggacaagggc   120
ttgagtggat gggatggatg aatccaaaca gtggagacac aggctttgca cagaaattcc   180
aggacagagt caccttgacc agaaacacgt ccattagcac agcctacatg agctgagca    240 gcctgagatc tgaagatacg gccgtctatt actgttcgag agccctcgt tacgattctt    300 ggagtggtta ttacagtgac ttctggggcc agggaaccct ggtcaccgtc tcctca       356

<210> SEQ ID NO 5
<211> LENGTH: 118
<212> TYPE: PRT
<213> ORGANISM: Homo sapiens

<400> SEQUENCE: 5

Gly Ala Gly Ala Glu Leu Lys Lys Pro Gly Ala Ser Val Lys Val Ser
1               5                   10                  15

Cys Lys Thr Ser Gly Tyr Ser Leu Thr Asn Tyr Gly Ile Asn Trp Val
            20                  25                  30

Arg Gln Ala Pro Gly Gln Gly Leu Glu Trp Met Ala Trp Ile Cys Gly
        35                  40                  45

Tyr Asn Gly Asp Thr Val Phe Ala Gln Lys Phe Gln Gly Arg Val Thr
    50                  55                  60

Met Thr Thr Asp Thr Ser Thr Asn Thr Val Tyr Met Asp Leu Arg Gly
65                  70                  75                  80

Leu Thr Ser Asp Asp Thr Ala Val Tyr Tyr Cys Ala Lys Glu Arg Arg
                85                  90                  95

Pro Phe Val Ala Pro Glu Gly Gly Met Asp Ala Trp Gly Gln Gly Thr
            100                 105                 110

Thr Val Thr Val Ser Ser
        115

<210> SEQ ID NO 6
<211> LENGTH: 356
<212> TYPE: DNA
<213> ORGANISM: Homo sapiens

<400> SEQUENCE: 6
atggagctgg ggctgagctg aagaagcctg gggcctcagt gaaggtctcc tgcaagactt    60
ctggttacag tttaaccaac tatggtatca actgggtgcg acaggccccc ggacaagggc   120
ttgagtggat ggcgtggatc tgcggttaca atggtgacac agtctttgca cagaagttcc   180
agggcagggt caccatgacc acagacacat ccacgaacac agtctacatg gacctgaggg   240
gcctgacatc tgacgacacg gccgtgtatt actgtgcgaa agagaggcgg ccgtttgtcg   300
caccagaagg aggtatggac gcctggggcc aagggacgac agtcaccgtc tcctca       356

<210> SEQ ID NO 7

```
<211> LENGTH: 117
<212> TYPE: PRT
<213> ORGANISM: Homo sapiens

<400> SEQUENCE: 7
```

| Gly | Val | Gly | Ala | Glu | Leu | Lys | Lys | Pro | Gly | Ser | Ser | Val | Lys | Val | Ser |
|---|---|---|---|---|---|---|---|---|---|---|---|---|---|---|---|
| 1 | | | | 5 | | | | | 10 | | | | | 15 | |

| Cys | Lys | Ala | Ser | Gly | Gly | Ser | Phe | Ala | Ser | Tyr | Ala | Ile | Ser | Trp | Val |
|---|---|---|---|---|---|---|---|---|---|---|---|---|---|---|---|
| | | | 20 | | | | | 25 | | | | | 30 | | |

| Arg | Gln | Ala | Pro | Gly | Gln | Gly | Leu | Glu | Trp | Met | Gly | Ala | Ile | Ile | Pro |
|---|---|---|---|---|---|---|---|---|---|---|---|---|---|---|---|
| | | | 35 | | | | | 40 | | | | | 45 | | |

| Val | Phe | Gly | Thr | Ala | Ser | Tyr | Ala | Gln | Gly | Phe | Gln | Gly | Arg | Val | Thr |
|---|---|---|---|---|---|---|---|---|---|---|---|---|---|---|---|
| | 50 | | | | | 55 | | | | | 60 | | | | |

| Ile | Ser | Ala | Asp | Lys | Ser | Thr | Asn | Val | Val | Asn | Met | Glu | Leu | Ser | Ser |
|---|---|---|---|---|---|---|---|---|---|---|---|---|---|---|---|
| 65 | | | | | 70 | | | | | 75 | | | | | 80 |

| Leu | Phe | Ser | Glu | Asp | Thr | Ala | Val | Tyr | Phe | Cys | Ala | Arg | Thr | Tyr | Met |
|---|---|---|---|---|---|---|---|---|---|---|---|---|---|---|---|
| | | | | 85 | | | | | 90 | | | | | 95 | |

| Trp | Asn | Thr | Gly | Asp | Trp | Phe | Phe | Asp | Leu | Trp | Gly | Arg | Gly | Thr | Leu |
|---|---|---|---|---|---|---|---|---|---|---|---|---|---|---|---|
| | | | 100 | | | | | 105 | | | | | 110 | | |

| Val | Thr | Val | Ser | Ser |
|---|---|---|---|---|
| | | | 115 | |

```
<210> SEQ ID NO 8
<211> LENGTH: 353
<212> TYPE: DNA
<213> ORGANISM: Homo sapiens
<400> SEQUENCE: 8
atggagttgg ggctgagctg aagaagcctg ggtcctcggt gaaggtctcc tgcaaggcct      60
ctggaggctc gttcgccagc tatgctatca gctgggtgcg acaggcccct ggacaagggc     120
ttgagtggat gggagcgatc atccctgtct ttggtacagc aagctacgca caggggttcc     180
aaggcagagt caccatttcc gcggacaaat ccacaaacgt agtcaacatg agctgagca      240
gcctgttttc tgaggacacg gccgtctatt tctgtgcgag acttacatg tggaacaccg      300
gggactggtt tttcgatctc tggggccgtg gcaccctggt cactgtctcc tca            353

<210> SEQ ID NO 9
<211> LENGTH: 114
<212> TYPE: PRT
<213> ORGANISM: Homo sapiens

<400> SEQUENCE: 9
```

| Gly | Ala | Gly | Ala | Glu | Leu | Val | Lys | Pro | Gly | Ala | Ser | Val | Lys | Leu | Ser |
|---|---|---|---|---|---|---|---|---|---|---|---|---|---|---|---|
| 1 | | | | 5 | | | | | 10 | | | | | 15 | |

| Cys | Lys | Ala | Ser | Gly | Tyr | Thr | Phe | Thr | Ser | Tyr | Trp | Met | His | Trp | Val |
|---|---|---|---|---|---|---|---|---|---|---|---|---|---|---|---|
| | | | 20 | | | | | 25 | | | | | 30 | | |

| Lys | Gln | Arg | Pro | Gly | Arg | Gly | Leu | Glu | Trp | Ile | Gly | Arg | Ile | Asp | Pro |
|---|---|---|---|---|---|---|---|---|---|---|---|---|---|---|---|
| | | | 35 | | | | | 40 | | | | | 45 | | |

| Asn | Ser | Gly | Gly | Thr | Lys | Tyr | Asn | Glu | Lys | Phe | Lys | Asn | Lys | Gly | Thr |
|---|---|---|---|---|---|---|---|---|---|---|---|---|---|---|---|
| | 50 | | | | | 55 | | | | | 60 | | | | |

| Leu | Thr | Val | Asp | Thr | Ser | Ser | Ser | Thr | Ala | Tyr | Met | His | Leu | Ser | Ser |
|---|---|---|---|---|---|---|---|---|---|---|---|---|---|---|---|
| 65 | | | | | 70 | | | | | 75 | | | | | 80 |

| Leu | Thr | Ser | Glu | Asp | Ser | Ala | Val | Tyr | Tyr | Cys | Thr | Arg | Glu | Leu | Pro |
|---|---|---|---|---|---|---|---|---|---|---|---|---|---|---|---|
| | | | | 85 | | | | | 90 | | | | | 95 | |

| Gly | Thr | Arg | Tyr | Phe | Asp | Val | Trp | Gly | Ala | Gly | Thr | Thr | Val | Thr | Val |
|---|---|---|---|---|---|---|---|---|---|---|---|---|---|---|---|
| | | | 100 | | | | | 105 | | | | | 110 | | |

Ser Ser

<210> SEQ ID NO 10
<211> LENGTH: 344
<212> TYPE: DNA
<213> ORGANISM: Homo sapiens

<400> SEQUENCE: 10

```
atggagctgg ggctgagctt gtgaagcctg gggcttcagt aaagctgtcc tgcaaggctt      60
ctggctacac cttcaccagc tactggatgc actgggtgaa gcagaggcct ggacgaggcc     120
tcgagtggat tggaaggatt gatcctaata gtggtggtac taagtacaat gagaagttca     180
agaacaaggg cacactgact gtagacacat cctccagcac agcctacatg cacctcagca     240
gcctgacatc tgaggactct gcggtctatt actgtacaag agaactacct gggacccggt     300
acttcgatgt ctggggcgca gggaccactg tcaccgtctc ctca                      344
```

OPSONIC AND PROTECTIVE MONOCLONAL ANTIBODIES AGAINST GRAM-POSITIVE PATHOGENS

CROSS REFERENCE TO A RELATED APPLICATION

This application is a National Stage Application of International Application Number PCT/EP2014/074797, filed Nov. 17, 2014; which claims priority to European Application No. 13199849.4, filed Dec. 30, 2013; which are incorporated herein by reference in their entirety.

The Sequence Listing for this application is labeled "SeqList-21Jun16.txt", which was created on Jun. 21, 2016, and is 9 KB. The entire content is incorporated herein by reference in its entirety.

The present invention in the fields of immunology and infectious diseases relates to opsonic and protective antibodies that are specific for Gram-positive bacteria, particularly to carbohydrate structures exposed on the surface of the bacteria. The invention includes monoclonal and chimeric antibodies, as well as fragments, regions and derivatives thereof. This invention also relates to the epitope to which the antibodies of the invention bind as well as the sequences, fragments, and regions of the epitopes. Both the antibodies and peptides that encompass the epitope, and regions and fragments thereof, may be used for diagnostic, prophylactic and therapeutic applications.

BACKGROUND OF THE INVENTION

Before the discovery and development of antibiotics, death due to a bacterial infection was frequently rapid and inevitable. Gram-positive multiresistant bacteria, such as *Staphylococcus aureus* and Enterococci , are among the major nosocomial pathogens and are responsible for numerous deaths and extended hospital stays of patients.

The cell walls of Gram-positive bacteria contain three major components: peptidoglycan, capsular polysaccharides, and teichoic acids plus additional carbohydrates, glycoconjugates and proteins depending on the species.

Of the Gram-positive bacteria, one of the most common genera is *Staphylococcus*. Staphylococci commonly colonize humans and animals and are an important cause of human morbidity and mortality, particularly in hospitalized patients. Staphylococci are prevalent on the skin and mucosal linings and, accordingly, are ideally situated to produce both localized and systemic infections.

Staphylococcal infections are difficult to treat for a variety of reasons. Resistance to antibiotics is common and becoming more so, due to transferrable methicillin and multidrug resistance. In addition, host resistance to Staphylococcal infections is still not clearly understood.

Opsonic antibodies have been proposed to prevent or treat Staphylococcal infections. See, for example, U.S. Pat. No. 5,571,511.

Enterococci are Gram-positive cocci that often occur in pairs ("diplococcus") or short chains, and are difficult to distinguish from "*Streptococcus*" on physical characteristics alone. Two species are common commensal organisms in the intestines of humans: *E. faecalis* (90-95%) and *E. faecium* (5-10%).

Important clinical infections caused by *Enterococcus* include urinary tract infections, bacteremia, bacterial endocarditis, diverticulitis, and meningitis. From a medical standpoint, an important feature of this genus is the high level of intrinsic antibiotic resistance. Some enterococci are intrinsically resistant to β-lactam-based antibiotics (penicillins, cephalosporins, carbapenems), as well as many aminoglycosides. In the last two decades, particularly virulent strains of *Enterococcus* that are resistant to vancomycin (vancomycin-resistant *Enterococcus*, or VRE) have emerged in nosocomial infections of hospitalized patients, especially in the US.

U.S. Pat. No. 4,578,458 describes a method of inducing an immune response against multiple strains of (the Gram-negative bacterium) *Pseudomonas aeruginosa* which comprises administering to a human or animal an amount of mucoid exopolysaccharide from *Pseudomonas aeruginosa* 2192 sufficient to induce an immune response in the human or animal is disclosed along with the microorganism which produces this antigen and a method of separating the antigen from the crude bacterial slime. Thus, a vaccine capable of inducing an immune response against multiple strains of *Pseudomonas aeruginosa* is provided. A minimum preferred amount is the amount required to elicit antibody formation to a concentration at least 4 times that which existed prior to administration.

U.S. Pat. No. 7,230,087 further describes peptides, particularly human monoclonal antibodies, that bind specifically to *Pseudomonas aeruginosa* mucoid exopolysaccharide. The invention further provides methods for using these peptides in the diagnosis, prophylaxis and therapy of *Pseudomonas aeruginosa* infection and related disorders (e.g., cystic fibrosis). Some antibodies of the invention enhance opsonophagocytic killing of multiple mucoid strains of *Pseudomonas aeruginosa*. Compositions of these peptides, including pharmaceutical compositions, are also provided, as are functionally equivalent variants of such peptides.

U.S. Pat. No. 5,233,024 describes an anti-idiotypic monoclonal antibody, which is opsonic for mucoid *Pseudomonas aeruginosa*. The anti-idiotypic monoclonal antibody is produced by a cell line designated C9F5 and having ATCC accession No. HB10715. The anti-idiotypic monoclonal antibody is useful as a vaccine and for diagnostic purposes.

WO 1998/57994 describes monoclonal and chimeric antibodies that bind to lipoteichoic acid of Gram-positive bacteria. The antibodies also bind to whole bacteria and enhance phagocytosis and killing of the bacteria in vitro and enhance protection from lethal infection in vivo. Here, a mouse monoclonal antibody that has been humanized is described. The publication also encompasses a peptide mimic of the lipoteichoic acid epitope binding site defined by the monoclonal antibody.

WO 2003/059260 discloses monoclonal antibodies that bind to lipoteichoic acid LTA of Gram-positive bacteria. The antibodies also bind to whole bacteria and enhance phagocytosis and killing of the bacteria in vitro. Described are also antibodies having human sequences chimeric, humanized and human antibodies.

EP2476702 A1 discloses monoclonal antibodies able to recognize and bind to PBP2a protein and other proteins presenting sequences homologous to PBP2a, including the pathogens methicillin-resistant *Staphylococcus aureus*—MRSA, coagulase-negative *Staphylococcus, Staphylococcus sciuri, Enterococcus* spp., and any other bacterium possessing PBP2a or sequences homologous to this protein. PBP2a is a class II multimodular enzyme anchored in the membrane of the bacteria and responsible for the bacterial transpeptidation reactions when synthesizing murein. The protection conferred by the treatment with monoclonal antibody caused a reduction of 89 times in the quantity of bacteria present in the kidneys of animals treated, which was higher than the protection obtained with the treatment with 5 vancomycin doses (reduction of 35 times). However, the most significant reduction result was seen in the group treated with antibody+vancomycin, causing a reduction of 450 times.

Theilacker et al. (in: Protection against *Staphylococcus aureus* by antibody to the polyglycerolphosphate backbone of heterologous lipoteichoic acid (LTA). J Infect Dis. 2012 Apr. 1; 205(7):1076-85) describe that antibodies against *E. faecalis* LTA also bind to type 1 LTA from other gram-positive species and opsonized *Staphylocccus epidermidis* and *Staphylcoccus aureus* strains as well as group B streptococci. Passive immunization with rabbit antibodies against *E. faecalis* LTA promoted the clearance of bacteremia by *E. faecalis* and *S. epidermidis* in mice. LTA is proposed as conserved bacterial structure that could function as a single vaccine antigen that targets multiple gram-positive pathogens.

WO 2005/103084 discloses human monoclonal antibodies that bind specifically to poly-N-acetyl glucosamine (PNAG), such as Staphylococcal PNAG, in acetylated, partially acetylated and/or fully deacetylated form. The antibodies can be used in the diagnosis, prophylaxis and therapy of infections by bacteria that express PNAG such as to Staphylococci and *E. coli*. Some antibodies of the invention enhance opsonophagocytic killing and in vivo protection against bacteria that express PNAG such as Staphylococci and *E. coli*.

WO 2007/141278 discloses single chain Fv fragments specifically binding to enterococci that are selected from scFv phage display libraries. An opsonophagocytic assay was conducted to quantify the killing activity of anti-enterococci human IgG1 against the enterococcal clinical isolate 12030. None of the antibodies as tested showed binding to lipoteichoic acid (LTA) of *S. aureus*.

The above state of the art shows that attempts were undertaken to produce more or less effective antibodies against a quite large variety of components of the cell wall of Gram-positive bacteria. Nevertheless, neither the target(s) nor the effectiveness of any of these antibodies in the protection against infections could be reliably predicted in advance.

There is a need in the art to provide new and effective monoclonal antibodies that can bind to *Staphylococcus* with higher affinity, and that can enhance phagocytosis and killing of the bacteria and thereby enhance protection in vivo. For the development of mAbs it would be advantageous to choose variable domains that recognize cross-reactive antigens to cover a broad spectrum of pathogens. There is a related need for humanized or other chimeric human/mouse monoclonal antibodies, and respective uses thereof in the treatment of Gram-positive infections.

SUMMARY OF THE INVENTION

To address these needs in the art, the present invention provides opsonic and protective monoclonal and chimeric antibodies that bind to Gram-positive bacteria. The antibodies also bind to whole bacteria and enhance phagocytosis and killing of the bacteria in vitro and enhance protection from prospectively lethal infection in vivo.

Accordingly, the invention provides broadly reactive and opsonic antibodies for the diagnosis, prevention, and/or treatment of bacterial infections caused by Gram-positive bacteria. The antibodies of the invention are broadly reactive with Gram-positive bacteria, meaning that they selectively recognize and bind to Gram-positive bacteria. Any conventional binding assay can be used to assess this binding, including for example, an enzyme linked immunosorbent assay. An important characteristic of the antibodies and antibody fragments provided by the invention is their ability to enhance opsonization and phagocytosis (i.e., opsonophagocytosis) of Gram-positive bacteria.

In one aspect, the invention provides an opsonic monoclonal antibody specific for Gram-positive bacteria, comprising at least one light chain and at least one heavy chain, wherein said at least one light chain comprises a polypeptide comprising an amino acid sequence having at least 80% identity with a light chain variable region selected from SEQ ID NO: 1, and wherein said at least one heavy chain comprises a polypeptide comprising an amino acid sequence having at least 80% identity with a heavy chain variable region selected from SEQ ID NOs: 3, 5, 7, and 9.

In one embodiment, the isolated peptide comprises an amino acid sequence of a heavy or light chain variable region of an antibody disclosed herein. In important embodiments, the amino acid sequences are selected from the group consisting of the light chain variable region selected from SEQ ID NO: 1, and the heavy chain variable region comprises a polypeptide comprising an amino acid sequence selected from SEQ ID NOs: 3, 5, 7, and 9.

Preferred are the specific antibodies of the present invention herein designated as VH2, VH3, VH4E, and VH8, respectively (in accordance with their heavy chains).

The peptides of the invention, including antibodies and antibody fragments, have particular utility in the detection of Gram-positive bacteria, the diagnosis of Gram-positive infection and the prevention and treatment of such infections and the disorders with which they are associated.

The selection process of the antibodies as described herein was carried out based on functions (i.e., uptake and killing of pathogens by phagocytes) and not—as in most approaches—on affinity. In the context of the present invention, opsonic and protective antibodies from a healthy individual were identified in order to target multiresistant pathogens. A pre-screen of a donor pool using an opsonophagocytic assay (OPA) with *E. faecalis* 12030 was used to identify the donor with the highest titers of opsonic antibodies. Whole blood was taken from that donor, and the B-cells were immortalized by infection with EBV. The immortalized B-cells were cultured until sufficient numbers for RNA preparations were achieved. The supernatant of each well was collected and used in an OPA against *E. faecalis* 12030 to identify the well resulting in the highest killing. B-cells from this well were in tissue culture wells. Supernatants were again tested by OPA and again the cells of the well leading to the highest killing were distributed into a new microtiter culture plate. After 4 rounds, B-cells in the wells with the strongest response were lyzed and mRNA and cDNA was prepared.

Using a degenerated primer set, variable domains (VH and VL) of the rearranged immunoglobulin, genes were amplified by PCR and cloned into a gram-positive expression vector containing the constant domain of a human IgG1 and human lambda constant domain for the light chain.

The plasmid containing the identified variable domain sequences were than transfected into chinese hamster ovary (CHO) cells and culture supernatants were collected, precipitated with ammonium sulfate, dialyzed and the concentration of antibody measured. The recombinant monoclonal antibody was tested by OPA against several *E. faecalis, E. faecium* and *S. aureus* strains. At concentrations of about 500-600 pg/ml, opsonic killing was between 40 and 70%.

A mouse sepsis model was used to assess protective efficacy and 4 µg/kg per mouse resulted in a statistically significant protection.

Preliminary experiments indicate that the antibodies specifically recognize non-proteinaceous and thus carbohydrate structures on the surface of the Gram-positive cells, which adds to their safety for use in the human patient.

The effectiveness of the present antibody is 1,000 times better than other anti-infective antibodies that are currently on the market [Andabaka T, Nickerson J W, Rojas-Reyes M X, Rueda J D, Bacic Vrca V, et al. (2013) Monoclonal antibody for reducing the risk of respiratory syncytial virus infection in children. Cochrane database of systematic reviews (Online) 4: CD006602. doi:10.1002/14651858.CD006602.pub4] or in development [Kelly-Quintos C, Cavacini L A, Posner M R, Goldmann D A, Pier G B (2006) Characterization of the opsonic and protective activity against Staphylococcus aureus of fully human monoclonal antibodies specific for the bacterial surface polysaccharide poly-N-acetylglucosamine. Infect Immun 74: 2742-2750. Wang W, Wang E Q, Balthasar J P (2008) Monoclonal Antibody Pharmacokinetics and Pharmacodynamics. Clin Pharmacol Ther 84: 548-558. Fox J L (2013) Anti-infective monoclonals step in where antimicrobials fail. Nat Biotechno131: 952-954.].

Thus, preferred is the monoclonal antibody according to the present invention, which, at concentrations of about 500-600 pg/ml, induces opsonic killing at between 40 and 70%, more preferably at between 60 and 70%.

Further preferred is the monoclonal antibody according to the present invention, which in a mouse sepsis model provides statistically significant protection at 4 µg/kg per mouse, more preferably at between 3 and 2 µg/kg per mouse.

Preferred is the monoclonal antibody according to the present invention, wherein the percentages identity are at least 90%, more preferably at least 95%, such as, for example, 98%. Most preferably, the variable regions of the monoclonal antibody according to the present invention consist of an amino acid sequence according to SEQ ID NO: 1, and an amino acid sequence selected from SEQ ID NOs: 3, 5, 7, and 9.

Included in the invention are also antibodies, wherein the variable regions of said antibody comprise and/or consist of an amino acid sequence according to SEQ ID NO: 1 (derived from DNA SEQ ID NO:2, wherein the percentages identity is at least 90%, more preferably at least 95%, such as, for example, 98%), and an amino acid sequence selected from SEQ ID NOs: 3, 5, 7, and 9, (derived from DNA SEQs ID NO:4, 6, 8, and 10, wherein the percentages identity are at least 90%, more preferably at least 95%, such as, for example, 98%) wherein some of the amino acids are modified because of post-translational modifications. These modifications include, for example, incomplete disulfide bond formation, glycosylation, N-terminal pyroglutamine cyclization, C-terminal lysine processing, deamidation, isomerization, and oxidation, and less common ones such as modification of the N-terminal amino acids by maleuric acid and amidation of the C-terminal amino acid. Modifications can be introduced in vitro and/or in vivo. Of course, according to the invention, these modified antibodies still enhance phagocytosis and killing of the bacteria in vitro and enhance protection from prospectively lethal infection in vivo.

An alternative embodiment is the monoclonal antibody according to the present invention, wherein at least one light chain, at least one heavy chain, or both are chimeric as described herein. More preferably, the monoclonal antibody according to the present invention comprises a heavy chain constant region, wherein said constant region comprises human IgG (all sub-types thereof), IgA, IgM, or IgD sequence, and/or comprises a light chain constant region comprising human kappa or lambda sequence.

In one embodiment, the isolated antibody or antibody fragment according to the present invention may be an isolated intact soluble monoclonal antibody. The isolated antibody or antibody fragment may be an isolated monoclonal antibody fragment selected from the group consisting of a Fab, Fab', F(ab')2, Fv, SFv, or scFv.

The antibodies of the present invention exhibit very strong binding (and thus have a high affinity), i.e., O.D.s of around twice background in an enzyme-linked immunosorbent assay against a test strain. In a preferred embodiment, the level of high binding is equal to or greater than five times background. In other embodiments, the level of high binding is equal to or greater than 10 times background. Of course, any meaningful increase over background (the level observed when all the reagents other than the antibody being tested) will be recognized by skilled persons in the art as high binding and therefore within the scope of the invention. Also as described in the state of the art, high binding has been found to correlate with opsonic activity.

The isolated antibody or antibody fragment according to the present invention enhances opsonophagocytosis of Gram-positive bacteria, such as Staphylococcus and/or Enterococcus. Such an antibody or antibody fragment is referred to herein as "an opsonic antibody or antibody fragment".

The antibodies of the invention are opsonic, or exhibit opsonic activity, for Gram positive bacteria. As those in the art recognize, "opsonic activity" refers to the ability of an opsonin (generally either an antibody or the serum factor C3b) to bind to an antigen to promote attachment of the antigen to the phagocyte and thereby enhance phagocytosis. Certain bacteria, especially encapsulated bacteria which resist phagocytosis due to the presence of the capsule, become extremely attractive to phagocytes such as neutrophils and macrophages when coated with an opsonic antibody and their rate of clearance from the bloodstream is strikingly enhanced. Opsonic activity may be measured in any conventional manner as described below, for example as described by Theilacker et al. (see below).

An opsonization assay can be a colorimetric assay, a chemiluminescent assay, a fluorescent or radiolabel uptake assay, a cell-mediated bactericidal assay, or any other appropriate assay known in the art which measures the opsonic potential of a substance and identifies broadly reactive immunoglobulin. In an opsonization assay, the following are incubated together: an infectious agent, a eukaryotic cell, and the opsonizing substance to be tested, or an opsonizing substance plus a purported opsonizing enhancing substance. Preferably, the opsonization assay is a cell-mediated bactericidal assay.

Alternatively, the opsonic ability is determined by measuring the numbers of viable organisms before and after incubation. A reduced number of bacteria after incubation in the presence of immunoglobulin indicates a positive opsonizing ability. In the cell-mediated bactericidal assay, positive opsonization is determined by culturing the incubation mixture under appropriate bacterial growth conditions. Any significant reduction in the number of viable bacteria comparing pre- and post-incubation samples, or between samples which contain immunoglobulin and those that do not, is a positive reaction.

Another preferred method of identifying agents for the treatment or prevention of an infection by Gram-positive bacteria employs animal models of sepsis or bacteremia that measure clearance and protection. Such agents can be immunoglobulin or other antimicrobial substances. A particularly useful animal model comprises administering an antibody and a Gram-positive organism to an immunocompromised (e.g., an immature) animal, followed by evaluating whether the antibody reduces mortality of the animal or enhances clearance of the organism from the animal. This assay may use any immature animal, including the rabbit, the guinea pig, the mouse, the rat, or any other suitable laboratory animal.

Clearance is evaluated by determining whether the pharmaceutical composition enhances clearance of the infectious agent from the animal. This is typically determined from a sample of biological fluid, such as blood, peritoneal fluid, or cerebrospinal fluid, or organs such as liver, spleen or kidney. The infectious agent is cultured from the biological fluid or organ in a manner suitable for growth or identification of the surviving infectious agent. From samples of fluid taken over a period of time after treatment, one skilled in the art can determine the effect of the pharmaceutical composition on the ability of the animal to clear the infectious agent. Further data may be obtained by measuring over a period of time, preferably a period of days, survival of animals to which the pharmaceutical composition is administered. Typically, both sets of data are utilized.

Results are considered positive if the pharmaceutical composition enhances clearance or decreases mortality. In situations in which there is enhanced organism clearance, but the test animals still perish, a positive result is still indicated.

The ability of the antibodies of the invention to bind to and opsonize Gram-positive bacteria, and thereby enhance phagocytosis and cell killing in vitro and to enhance protection in vivo is unexpected.

With this level of opsonic activity, an antibody should enhance phagocytosis and cell killing of both coagulase-negative and coagulase-positive staphylococci. The term "enhanced" refers to activity that measurably exceeds background at a valuable level. The level deemed valuable may well vary depending on the specific circumstances of the infection, including the type of bacteria and the severity of the infection. For example, for enhanced opsonic or phagocytic activity, in a preferred embodiment, an enhanced response is equal to or greater than 75% over background. In another preferred embodiment, the enhanced response is equal to or greater than 80% over background. In yet another embodiment, the enhanced response is equal to or greater than 90% over background.

To confirm that the antibody, shown to be opsonic, would be protective in vivo, it was assessed in an infection model in mice and an endocarditis model in rats. As set forth in the Examples, the antibodies markedly enhance the clearance of bacteria from the blood stream and from internal organs (such as liver, kidneys, and spleen) and from cardiac vegetations.

These antibodies of the present invention include polyclonal antibodies as well as monoclonal antibodies, as well as other monoclonal antibodies, fragments and regions thereof, as well as derivatives thereof. As set forth above, the strength of the binding may range from twice above background, to five- and ten-times above background.

In addition, the antibodies, fragments, regions, and derivatives of the present invention are capable of enhancing the opsonization of such bacteria, at rates ranging from 75% and up. The "fragments" of the antibodies of the invention include, for example, Fab, Fab', F(ab')2, and scFv. These fragments are produced from intact antibodies using methods well known in the art such as, for example, proteolytic cleavage with enzymes such as papain (to produce Fab fragments) or pepsin (to produce F(ab')2).

In a preferred aspect of the invention, the regions include at least one heavy chain variable region or a light chain variable region which binds a Gram-positive bacterium. In another embodiment, these two variable regions can be linked together as a single chain antibody. While a full length heavy chain may be critical for opsonic activity and enhance anti-cytokine (anti-inflammatory) activity, the antibody fragments encompassing the variable regions may be suitable for inhibition of bacterial binding to epithelial cells and may also be anti-inflammatory.

In a particularly preferred aspect of the invention, the antibody is a recombinant human anti-body made up of regions from the antibodies of the invention together with constant regions of human antibodies (IgG). For example, an H chain can comprise the antigen-binding region of the heavy chain variable region of an antibody of the invention linked to at least a portion of a human heavy chain constant region. This humanized or chimeric heavy chain may be combined with a chimeric L chain that comprises the antigen binding region of the light chain variable region of the antibody linked to at least a portion of the human light chain constant region.

The recombinant antibodies of the invention may be monovalent, divalent, or polyvalent immunoglobulins. For example, a monovalent antibody is a dimer (HL) formed by an H chain associated through disulfide bridges with an L chain, as noted above. A divalent antibody is a tetramer formed by two HL dimers associated through at least one disulfide bridge. A polyvalent antibody is based on an aggregation of chains.

Particularly preferred antibodies of the invention are described in the Examples, and comprise i) a light chain comprising a sequence according to SEQ ID No: 1, and a heavy chain comprising a sequence according to SEQ ID No: 3, ii) a light chain comprising a sequence according to SEQ ID No: 1, and a heavy chain comprising a sequence according to SEQ ID No: 5, iii) a light chain comprising a sequence according to SEQ ID No: 1, and a heavy chain comprising a sequence according to SEQ ID No: 7, and iv) a light chain comprising a sequence according to SEQ ID No: 1, and a heavy chain comprising a sequence according to SEQ ID No: 9.

Of course, other recombinant antibodies composed of different sections of the antibodies of the invention are within the invention. In particular, the heavy chain constant region can be an IgG2, IgG3, IgG4, IgM or IgA antibody.

The Gram-positive bacterial infection to be treated or prevented can be selected from the group consisting of *Staphylococcus epidermidis, Staphylococcus hemolyticus, Staphylococcus hominus, Staphylococcus aureus, Streptococcus mutans, Enterococcus faecalis* or *Enterococcus faecium*, and *Streptococcus pyogenes* or *Streptococcus pneumoniae*.

Another aspect of the monoclonal antibody according to the present invention then relates to an antibody, wherein said monoclonal antibody or antigen-binding fragment thereof is conjugated to a detectable label. Labels suitable for use in detection of a complex between an epitope, bacterium and an antibody or antigen-binding fragment of the invention include, for example, a radioisotope, an epitope label (tag), an affinity label (e.g., biotin, avidin), a spin label, an enzyme, a toxin, or a fluorescent group or a chemiluminescent group.

In another aspect of the invention, the invention also encompasses an isolated nucleic acid encoding for monoclonal antibody or a fragment thereof as described above. The nucleic acid can be selected from RNA, DNA, PNA, and/or cDNA. The nucleic acid(s) of the invention can be isolated and/or cloned in vectors, such as plasmids, for example expression vectors. Thus, in addition to the protein fragments and regions of the antibodies, the present invention also encompasses the DNA sequence of the gene coding for the antibodies as well as the peptides encoded by said DNA.

Particularly preferred DNA and peptide sequences are set forth in the Figures and the attached sequence listing, in particular in SEQ ID NO: 1, 3, 5, 7, and 9 (for peptides), and SEQ ID NO: 2, 4, 6, 8, and 10 (for nucleic acids), describing the variable regions of both the heavy and light chains of preferred antibodies, including the Complementarity Determining Regions ("CDR"), the hypervariable amino acid sequences within antibody variable regions which interact with amino acids on the complementary antigen.

The invention includes these DNA and peptide sequences as well as DNA and peptide sequences that are homologous (share identity) to these sequences. In a preferred embodiment, these sequences are 80% homologous although other preferred embodiments include sequences that are 85%, 90%, and 95% homologous. Determining these levels of homology for both the DNA and peptide sequence is well within the routine skill of those in the art.

The DNA sequences of the invention can be identified, isolated, cloned, and transferred to a prokaryotic or eukaryotic cell for expression by procedures well-known in the art. Such procedures are generally described in Sambrook et al., supra, as well as Current Protocols in Molecular Biology (Ausubel et al., eds., John Wiley & Sons), incorporated by reference.

In addition, the DNA and peptide sequences of the antibodies of the invention, including both monoclonal and chimeric antibodies, may form the basis of antibody "derivatives", which include, for example, the proteins or peptides encoded by truncated or modified genes. Such proteins or peptides may function similarly to the antibodies of the invention. Other modifications, such as the addition of other sequences that may enhance the effector function, which includes phagocytosis and/or killing of the bacteria, are also within the present invention.

In another aspect of the invention, the invention also encompasses a hybridoma cell line expressing a monoclonal antibody according to the present invention. Generally, a hybridoma is produced by fusing a suitable immortal cell line (e.g., a myeloma cell line) with antibody-producing cells. Antibody-producing cells can be obtained from the peripheral blood or, preferably the spleen or lymph nodes, of humans or other suitable animals immunized with the antigen of interest. The fused cells (hybridomas) can be isolated using selective culture conditions, and cloned by limiting dilution. Cells that produce antibodies with the desired specificity can be selected by a suitable assay (e.g., ELISA).

The present invention also discloses a pharmaceutical composition comprising an antibody of the invention, monoclonal or chimeric, as well as fragments, regions, and derivatives thereof, together with a pharmaceutically acceptable carrier.

Pharmaceutically acceptable carriers can be sterile liquids, such as water, oils, including petroleum oil, animal oil, vegetable oil, peanut oil, soybean oil, mineral oil, sesame oil, and the like. With intravenous administration, water is a preferred carrier. Saline solutions, aqueous dextrose, and glycerol solutions can also be employed as liquid carriers, particularly for injectable solutions. Suitable pharmaceutical carriers are described in Remington's Pharmaceutical Sciences, 22nd Edition (2012), incorporated by reference.

Preferred is a pharmaceutical composition according to the present invention, which is for i.v., intraperitoneal (i.p.), or internasal administration. Administering the pharmaceutical composition (including antibodies) can also be achieved by intravenous, intraperitoneal, intracorporeal injection, intra-articular, intraventricular, intrathecal, intramuscular, subcutaneous, intranasally, intravaginally, orally, or by any other effective method of administration. The composition may also be given locally, such as by injection to the particular area infected, either intramuscularly or subcutaneously. Administration can comprise administering the pharmaceutical composition by swabbing, immersing, soaking, or wiping directly to a patient. The pharmaceutical composition can also be applied to objects to be placed within a patient, such as dwelling catheters, cardiac values, cerebrospinal fluid shunts, joint prostheses, other implants into the body, or any other objects, instruments, or appliances at risk of becoming infected with a Gram-positive bacteria, or at risk of introducing such an infection into a patient.

Finally, the present invention provides methods for treating or preventing infections caused by Gram-positive bacteria comprising administering to the patient a therapeutically or prophylactically effective amount of the pharmaceutical composition according to the present invention, wherein the patient is infected with, or suspected of being infected with, a Gram-positive bacteria, such as a staphylococcal or enterococcal organism. The method comprises administering a therapeutically effective amount of a pharmaceutical composition comprising the monoclonal or chimeric antibody of the invention, including fragments, regions, and derivatives thereof, and a pharmaceutically acceptable carrier. A patient can be a human or other mammal, such as a dog, cat, cow, sheep, pig, or goat. The patient is preferably a human.

A therapeutically effective amount is an amount reasonably believed to provide some measure of relief or assistance in the treatment of the infection. Such therapy as above or as described below may be primary or supplemental to additional treatment, such as antibiotic therapy, for a staphylococcal or enterococcal infection, an infection caused by a different agent, or an unrelated disease. Indeed, combination therapy with other antibodies is expressly contemplated within the invention.

A prophylactically effective amount is an amount reasonably believed to provide some measure of prevention of infection by Gram-positive bacteria. Such therapy as above or as described below may be primary or supplemental to additional treatment, such as antibiotic therapy, for a staphylococcal infection, an infection caused by a different agent, or an unrelated disease. Indeed, combination therapy with other antibodies is expressly contemplated within the invention.

The Gram positive bacterium to be treated or prevented is selected from the group consisting of *Staphylococcus epidermidis, Staphylococcus hemolyticus, Staphylococcus hominus, Staphylococcus aureus, Streptococcus mutans, Enterococcus faecalis* or *Enterococcus feacium*, and *Streptococcus pyogenes, Streptococcus pneumoniae* or *Streptococcus agalactiae*.

In a preferred embodiment of the method of the invention, the Gram-positive bacteria are antibiotic resistant, such as MRSA, VRSA, MDR or VRE.

Yet another aspect of the invention relates to a method for detecting a Gram-positive bacterium in a subject comprising determining a test level of binding of the isolated anti-Gram positive monoclonal antibody according to the present invention, or an antigen-binding fragment thereof, to a sample from a subject, and comparing the test level of binding to a control, wherein a test level of binding that is greater than the control is indicative of the presence of a Gram-positive bacterium in the sample.

The invention relates to a selection method for identifying of protective human monoclonal antibodies as well as the identification of four candidate-antibodies for the prophylaxis, therapy and diagnosis of enterococcal and staphylococcal infections. For this, blood was taken from a group of healthy volunteers, and the serum was analyzed for opsonic activity. A donor having high opsonic killing was selected, blood was drawn, and the B-cells in the whole blood were immortalized using EBV. The immortalized B-cells were dispersed onto a cell culture plate, and cultured. The cell culture supernatants were analyzed by means of an opsonophagocytotic assay, and those wells were identified that showed the highest killing. All B-cells that grew in this well were then dispersed onto another microtiter plate, and again the well with the best killing was identified and re-seeded. After four rounds total RNA was isolated from the best well, and transcribed into cDNA. Using a set of primers (see reference 1) the variable domains of the heavy and light antibody chains were amplified, and cloned into a eukaryotic expression vector. It was found that four different antibodies were present in the well, and that all antibodies had the same light chain (SEQ ID No: 1). The four constructs were transfected into CHO cells, and the recombinant human monoclonal antibodies were purified from the supernatant. These antibodies were then tested in an opsonophagocytosis-assay, and exhibited killing in a concentration of 50-500 ng/ml, whereby a killing of the antibodies was found both against the tested several *E. faecalis, E. faecium* and *S. aureus* strains. Then, the antibodies were tested further in an in vivo mouse and rat model.

The invention will now be further described in the following examples, of course, these are included only for purposes of illustration and are not intended to be limiting of the present invention. For the purposes of the present invention, all references as cited are herein incorporated by reference in their entireties. The Figures and the attached sequence listing show:

FIG. 1: The results of the opsophagocytic assays using the antibodies according to the present invention with *E. faecium* E1162. F428 indicates the control using the *P. aeruginosa* mucoid exopolysaccharide specific binding antibody as described in U.S. Pat. No. 7,119,172.

Figure 2:
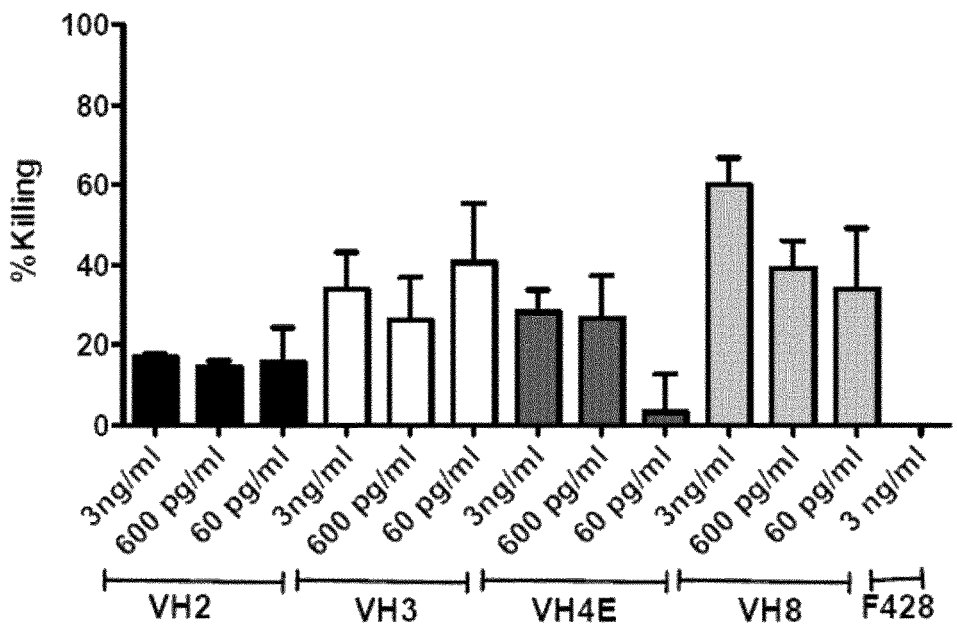

FIG. 2: The results of the opsophagocytic assays using the antibodies according to the present invention with the *E. faecium* patient isolate. F428 is as in FIG. 1.

Figure 3:
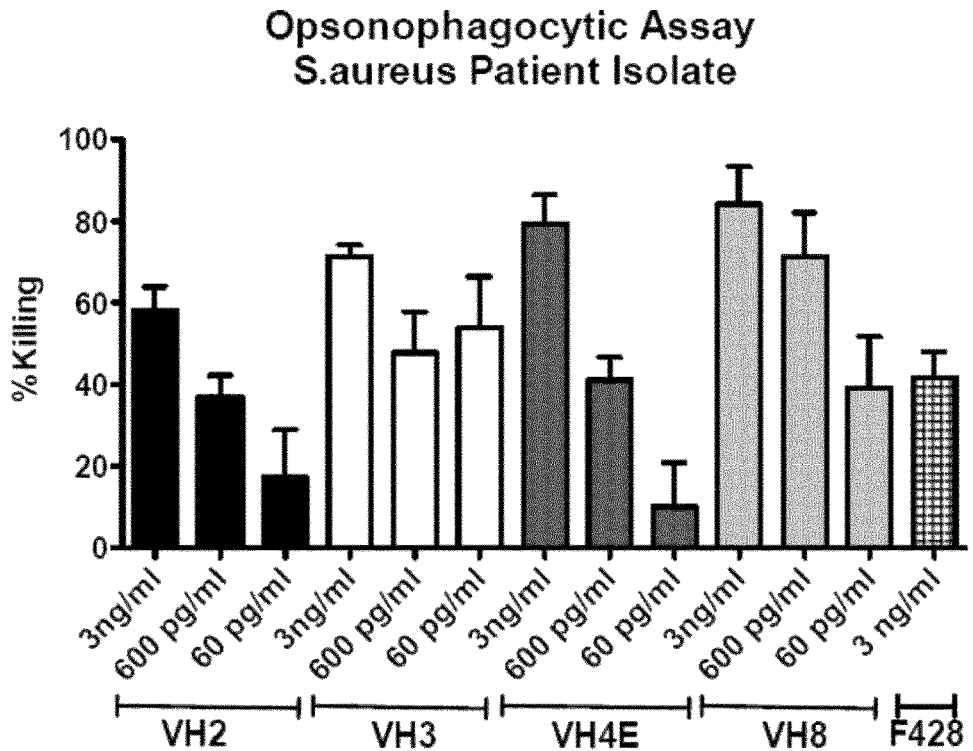

FIG. 3: The results of the opsophagocytic assays using the antibodies according to the present invention with the *S. aureus* patient isolate. F428 is as in FIG. 1.

Figure 4:
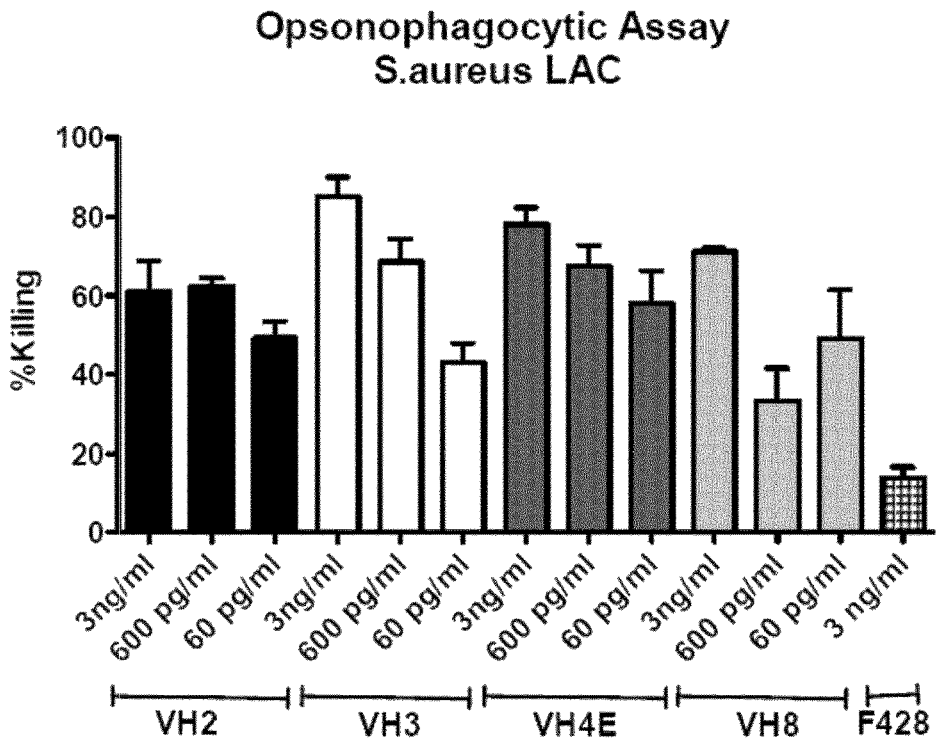

FIG. 4: The results of the opsophagocytic assays using the antibodies according to the present invention with the *S. aureus* LAC. F428 is as in FIG. 1.

Figure 5:
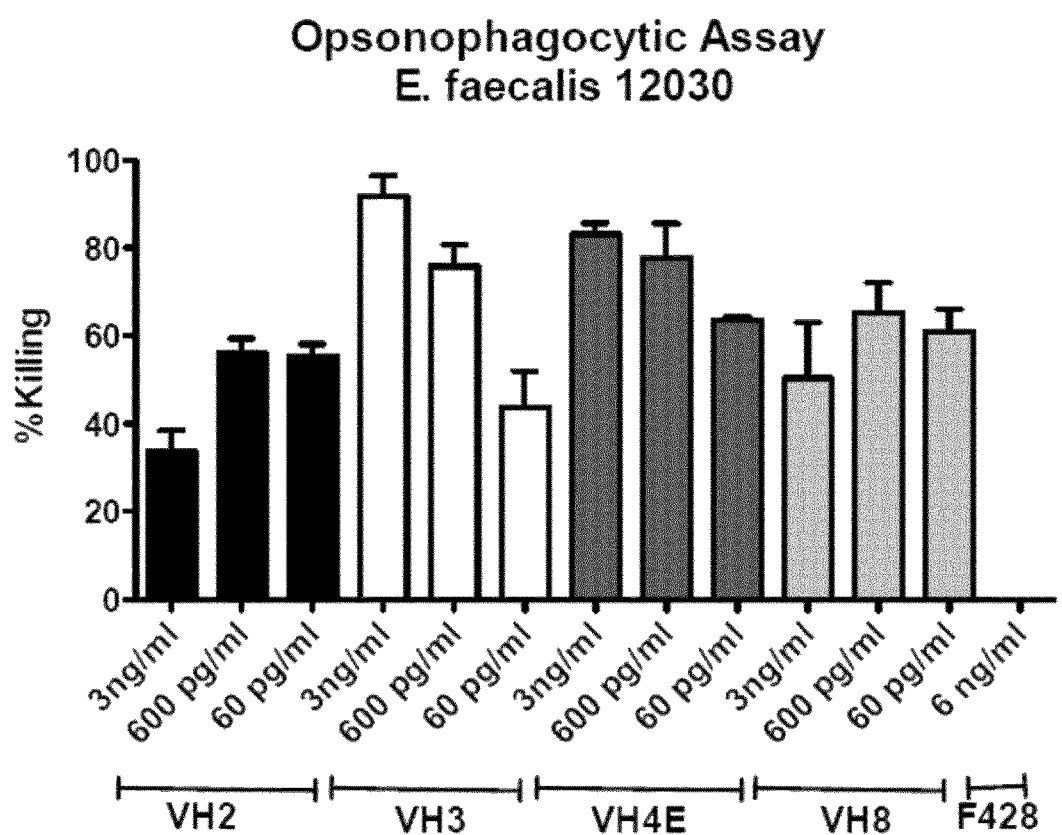

FIG. 5: The results of the opsophagocytic assays using the antibodies according to the present invention with *E. faecalis* 12030. F428 is as in FIG. 1.

Figure 6:
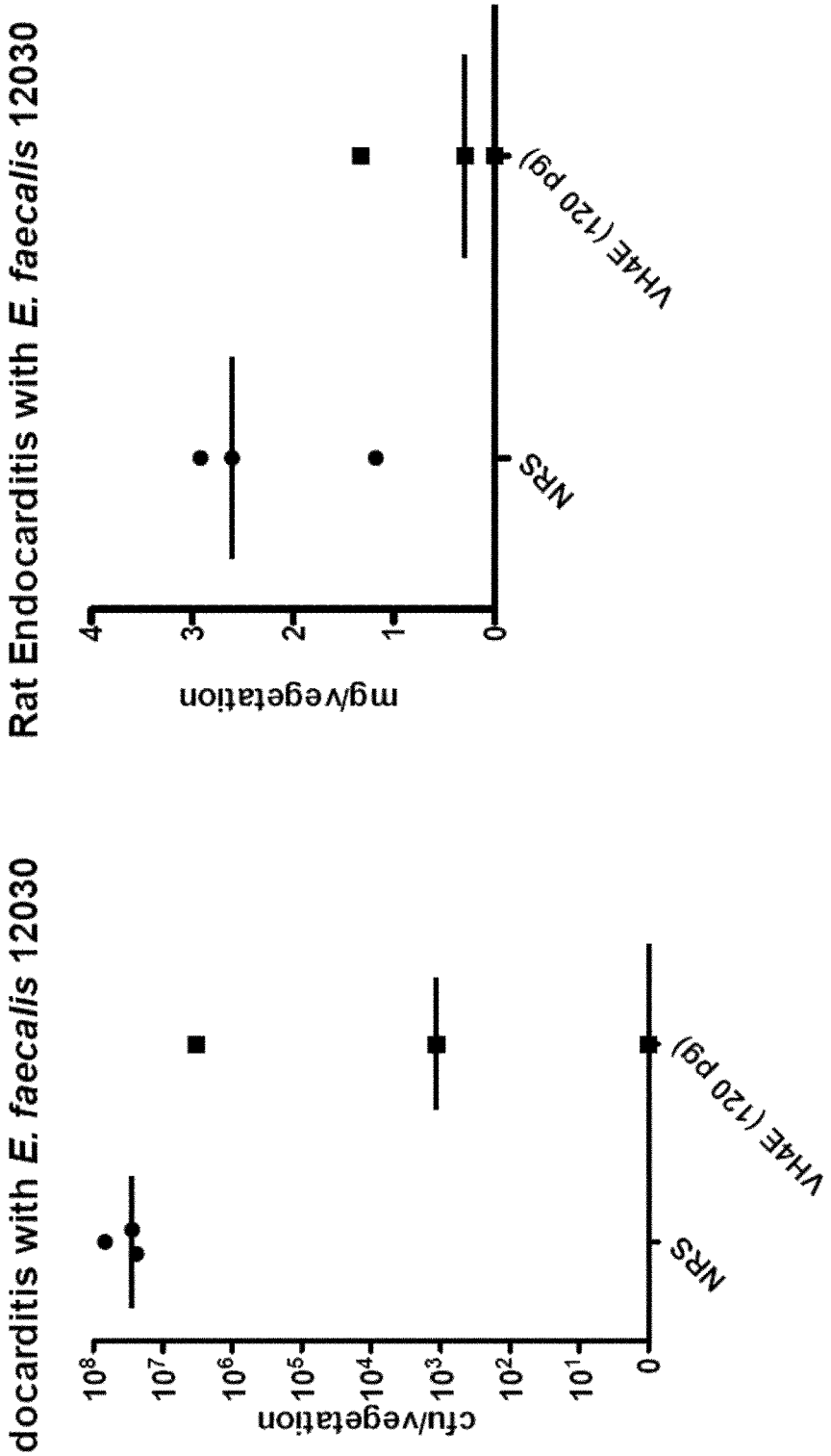

FIG. 6: The results of the rat endocarditis test with *E. faecalis* 12030. Rat endocarditis model was performed as described by Haller C et al. and confirms protection against *E. faecalis* 12030 in an independent animal model.

Figure 7:
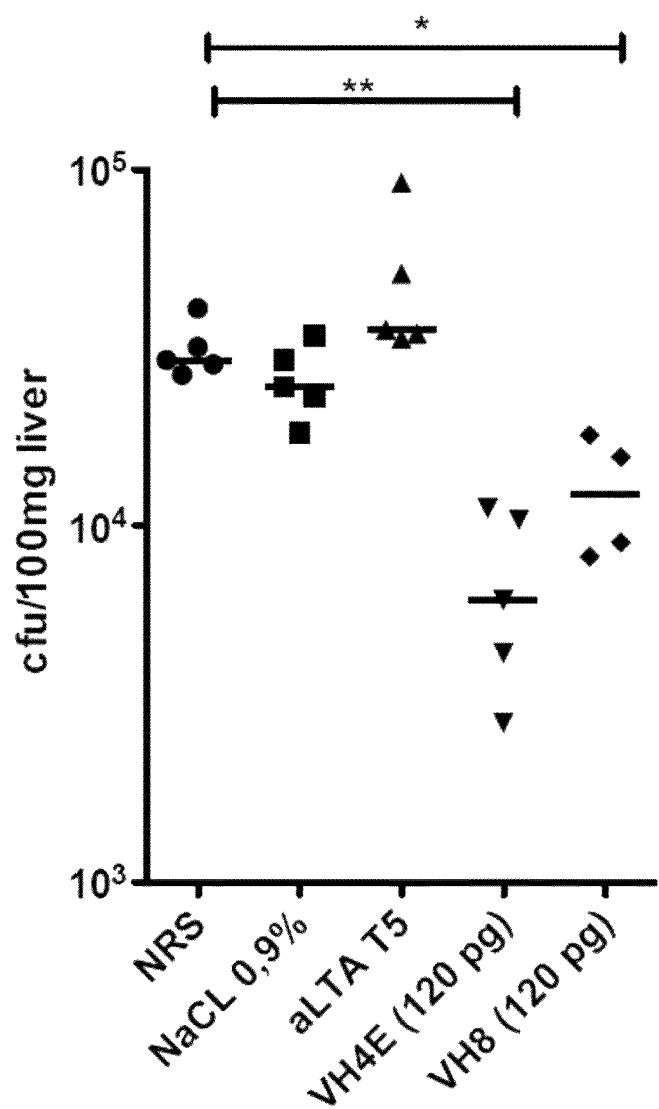

FIG. 7: The results of a mouse bacteremia model displaying colony counts in the liver with *S. aureus* LAC. Bacteria mouse sepsis was performed as described by Bao et al. showing that VH4E and VH8 are protective in a mouse model against both strains.

Figure 8:
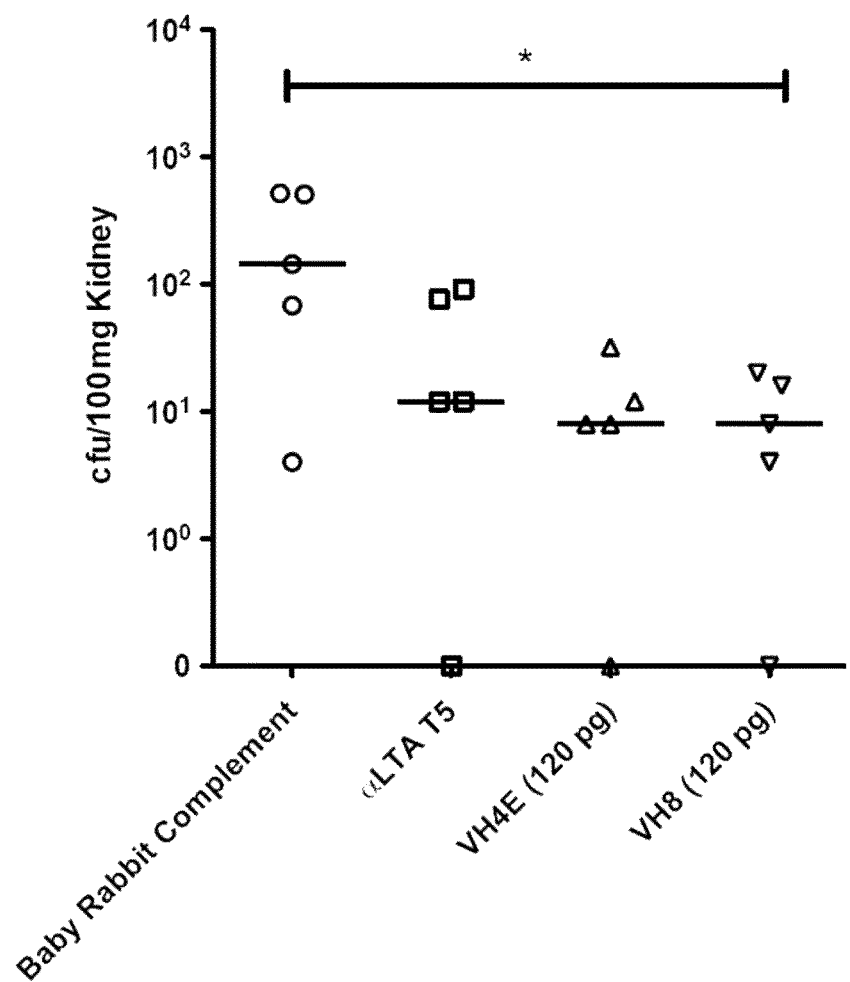

FIG. 8: The results of the mouse bacteremia model with *E. faecalis* E1162.

Figure 9:
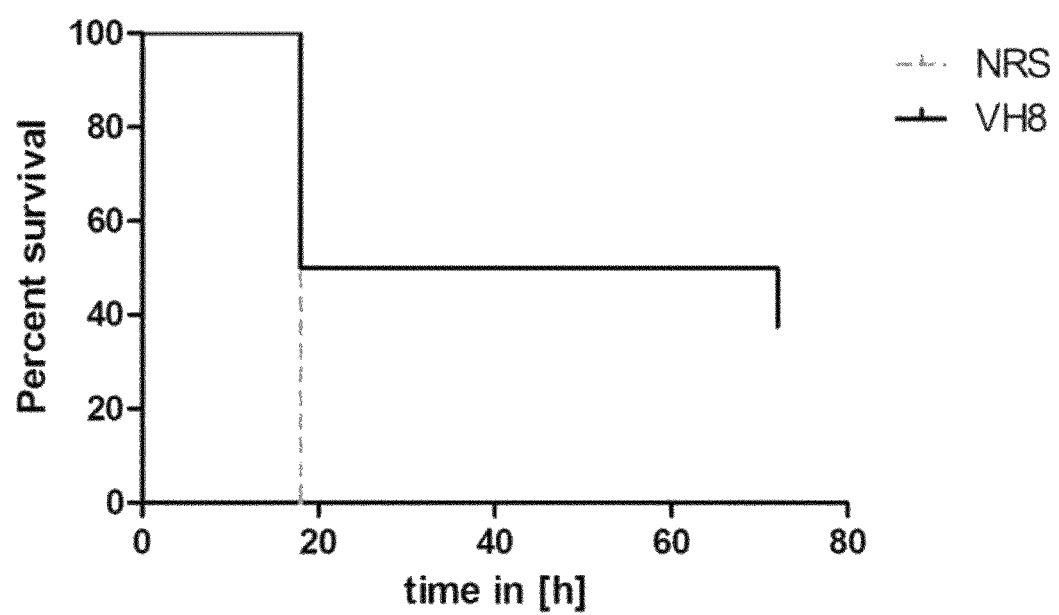

FIG. 9: Protection against *S. aureus* Newman infection with IgG1 mAbs (10 mice per group). A dose of 4 µg/kg of mAb VH8 and 200 µl of Normal Rabit Serum (NRS) as a control were administered 24 hours before bacterial challenge. Strain Newman was used at a challenge dose of $2 \times 10^8$ cfu/mouse.

SEQ ID NO: 1: peptide sequence of the light chain of the antibodies as identified according to the present invention.

SEQ ID NO: 3, 5, 7, and 9: peptide sequences of the heavy chains of the antibodies as identified according to the present invention.

SEQ ID NO: 2: nucleotide sequence of the light chain of the antibodies as identified according to the present invention.

SEQ ID NO: 4, 6, 8, and 10: nucleotide sequences of the heavy chains of the antibodies as identified according to the present invention.

EXAMPLES

Summary

Opsonic and protective antibodies from a healthy individual were identified to target multiresistant pathogens. A pre-screen of a donor pool using an opsonophagocytic assay (OPA) with *E. faecalis* 12030 was used to identify the donor with the highest titers of opsonic antibodies. Ten milliliter of whole blood were taken from that donor and the B-cells were immortalized by infection with EBV. The immortalized B-cells were cultured in 48-well plates for ca. 8 weeks until sufficient numbers for RNA preparations were achieved. The supernatant of each well was collected and used in an OPA against *E. faecalis* 12030 to identify the well resulting in the highest killing. B-cells from this well were distributed into a new 48-well tissue culture plate. Supernatants were again tested by OPA and again the cells of the well leading to the highest killing were distributed into a new 48-well plate. After 4 rounds, B-cells in the wells with the strongest response were lyzed and mRNA and cDNA was prepared. Using a degenerated primer set, variable domains (VH and VL) of the rearranged immunoglobulin, genes were amplified by PCR and cloned into a gram-positive expression vector containing the constant domain of a human IgG1 and human lambda constant domain for the light chain[1]. The plasmid containing the identified variable domain sequence was than transfected into CHO cells and culture supernatants were collected, precipitated with ammonium sulfate, dialyzed and the concentration of antibody measured. The recombinant monoclonal antibody was tested by OPA against several *E. faecalis, E. faecium* and *S. aureus* strains. At concentrations of about 500-600 pg/ml, opsonic killing was between 40 and 70%. A mouse sepsis model was used to assess protective efficacy and 4 µg/kg per mouse resulted in a statistically significant protection.

Bacterial Strains and Plasmids

*E. coli* were grown with agitation at 37° C. in Luria broth (LB; Roth) or LB Agar, while gram-positive bacteria (*S. aureus, E. faecalis* and *E. faecium*) were grown in Tryptic Soy Broth (TSB) or Tryptic Soy Agar (TSA) at 37° C. without agitation. Antibiotics (all purchased from Sigma) were added as indicated.

EBV Immortalization and Identification of Opsonic B-cell Clones

Blood (10 ml) was taken by venipuncture from healthy volunteers and B-cells were isolated and immortalized as described by Tosato et al. Immortalized cells were cultured in tissue culture plates for 6 days and then stimulated by 40 μg/ml TNP-LPS (Biosearch Technologies), 10 U/ml hIl-1 (BD) and 100 U/ml hIl-2 (BD). The supernatant of each well was collected and used in an opsonophagocytic killing assay (OPA) against *E. faecalis* 12030 to identify the well resulting in the highest killing. B-cells from this well were distributed into a new tissue culture plate. Supernatants were again tested by OPA and the cells of the well leading to the highest killing were distributed into a new plate. After 4 rounds, B-cells in the wells with the strongest response were lyzed and mRNA and cDNA was prepared.

Amplification of Variable Domains

Immortalized B-cells were cultured after the final round of selection for about 8 weeks until sufficient numbers for RNA preparations were obtained. RNA was extracted from about $5 \times 10^6$ immortalized cells using the RNeasy kit (QIAGEN) according to the manufacturer's instructions. A 500 ng volume of total RNA was reverse transcribed using the Omniscript kit (QIAGEN) and 1 .mu.l volume of the cDNA product was used as a template for PCRs. Each reaction consisted of 50 .mu.l PCR Mix (HotStart Taq DANN Polymerase, QIAGEN), 100 pmol of each primer, and 1 .mu.l cDNA template. For PCR amplification 35 cycles were used with the following protocol: 95.degree. C. for 30 s initially followed by cycles of 95.degree. C. for 30 s, 58.degree. C. for 30 s, and 68.degree. C. for 45 s, with a final extension at 70.degree. C. for 10 min. PCR products were cloned into the TOPO cloning vector 2.1 (Invitrogen) and sequenced. The resultant sequences were compared against known germ line sequences using IgBLAST.

Cloning of Variable Domains into Eukaryotic Expression Vector TCAE6.7

The TCAE6.7 vector containing the human lambda and IgG1 constant region was used as previously described [Preston M J, Gerceker A A, Reff M E, Pier G B (1998) Production and characterization of a set of mouse-human chimeric immunoglobulin G (IgG) subclass and IgA monoclonal antibodies with identical variable regions specific for *Pseudomonas aeruginosa* serogroup O6 lipopolysaccharide. Infect Immun 66: 4137-4142. Pier G B, Boyer D, Preston M, Coleman F T, Llosa N, et al. (2004) Human monoclonal antibodies to *Pseudomonas aeruginosa* alginate that protect against infection by both mucoid and nonmucoid strains. J Immunol 173: 5671-5678]. Heavy (H) chain V-region genes from the four constructs were digested with SalI and NheI restriction enzymes (NEB) and ligated into TCAE6.7 cut with the same enzymes. The ligation reaction mixture was transformed into competent *E. coli* TOP10 cells (Invitrogen) and plasmids were purified using a plasmid Miniprep kit (QIAGEN). The vector was sequenced to confirm the correct sequence. For light (L) chains, variable domains of the light chain cloned into the TOPO cloning vector 2.1 were digested with BglII and AvrII restriction enzymes (NEB) and ligated with the TCAE6.7 vector already containing the matching H chain variable region and cut with the same enzymes. Plasmids were transformed into *E. coli* TOP10 cells (Invitrogen), individual colonies were isolated, plasmids were obtained, and the inserted DNA was sequenced to ensure that the correct L chain V region was cloned into the eukaryotic expression vector. Since IgG1 has been reported to be superior to IgG3 in complement-mediated killing of bacteria [Brüggemann M, Williams G T, Bindon C I, Clark M R, Walker M R, et al. (1987) Comparison of the effector functions of human immunoglobulins using a matched set of chimeric antibodies. J Exp Med 166: 1351-1361], the inventors used IgG1 constant domains.

Transfection of CHO Cells and Expression of the Recombinant Antibody Molecules

Four constructs containing the different H chains (VH2, VH3, VH4E and VH8, see sequences as herein) combined with the L chain were created and were transfected separately into Chinese Hamster Ovary (CHO) DHFR-/- cells by using Lipofectamine 2000 (Invitrogen) according to the manufacturer's instructions. Stably transfected cells were selected using medium without nucleotides (Biochrom). Culture supernatants of the transfected CHO cells were harvested daily for 8 days. Supernatants containing monoclonal antibodies were pooled, precipitated with ammonium sulfate (35% w/v), washed and dialyzed against phosphate-buffered saline (PBS) (Biochrom) using Slide-A-Lyzer dialysis cassettes (MWCO 10; Thermo Scientific). Monoclonal antibody (mAb) concentrations were determined by ELISA using the standards and the kit from General Bioscience.

Opsonophagocytic Assay (FIGS. 1 to 5) Opsonophagocytic killing was measured as described by Theilacker et al. (1, 2) using 1.7% baby rabbit serum (Cedar Lane) as complement source and rabbit sera raised against purified lipoteichoic acid (LTA) from *E. faecalis* 12030 as positive control (3-5). Bacteria were incubated and grown to mid-exponential ($OD_{650\,nm}$) phase. Equal volumes of bacterial suspension ($2.5 \times 10^7$ per ml), leukocytes ($2.5 \times 10^7$ per ml), complement source (1.7% final concentration), and heat-inactivated immune rabbit serum at the dilutions indicated were combined and incubated on a rotor rack at 37° C. for 90 minutes. After incubation, live bacteria were quantified by agar culture of serial dilutions. Percent of killing was calculated by comparing the colony counts at 90 min (t90) of a control not containing PMNs ($PMN^{neg}$) to the colony counts of a tube that contained all four components of the assay using the following formula:

$$\{[(\text{mean CFU PMN}^{neg} \text{ at t90}) - (\text{mean CFU at t90})] / (\text{mean CFU PMN}^{neg} \text{ at t90})\} \times 100.$$

Opsonophagocytic killing of bacteria by monoclonal antibodies VH2, VH3, VH4E and VH8 was evaluated. Monoclonal antibody F1428 was used as a control and targets alginate in *Pseudomonas aeruginosa* (Pier Preston JI 2004). Opsonophagocytic killing of 5 strains—*E. faecalis* 12030, *E. faecium* 1162 (VRE), *E. faecium* (patient isolate), *S. aureus* LAC (MRSA) and *S. aureus* (patient isolate)—occurred in the presence of monoclonal antibodies in a dose-dependent manner, whereas the control monoclonal antibody F428, neutrophils and complement alone did not reduce viable counts.

Animal Experiments (FIGS. 6 to 9)

The protective efficacy of the monoclonal antibodies was tested against *E. faecalis* 12030 and *S. aureus* LAC in a mouse bacteremia model as described previously (3). Eight female BALB/c mice 6-8 weeks old (Charles River Laboratories Germany GmbH) were infected by i.v. injection of *E. faecalis* 12030 ($1.8 \times 10^8$ cfu) or *S. aureus* ($5.0 \times 10^7$ cfu) via the tail vein. Fourty-eight hours after infection, mice were sacrificed and organs were aseptically removed, weighted and homogenized. Bacterial counts were enumerated by serial dilutions on TSA plates after overnight incubation. Statistical significance was assessed by Mann-Whitney test.

Passive immunization with monoclonal antibodies VH4E and VH8 promotes clearance of Enterococcus faecium E1162 and Staphylococcus aureus LAC from the bloodstream, whereas non-immune rabbit sera (NRS) did not protect from bacterial bloodstream infection after 24 hours. A lipoteichoic acid-specific serum (αLTA T5) was used as a positive control because the inventors have shown previously that this serum is opsonic and protective against these strains (4).

Female Wistar rats (Charles River Laboratories Germany GmbH), weighing 200 to 300 g were used in a rat endocarditis model. The animals were anesthetized by subcutaneous application of 5.75% ketamine and 0.2% xylazine. Nonbacterial thrombotic endocarditis was caused by insertion of a small plastic catheter (polyethylene tubing; Intramedic PE 10) via the right carotid artery. The polyethylene catheter was introduced and advanced through the aortic valve into the left ventricle and proper placement was ensured via invasive pressure measurement through the catheter's lumen. The catheter was secured in place and distally ligated. Inoculation of bacteria followed 48 h after catheter placement via injection into the tail vein. Rats were assigned to two groups and challenged with E. faecalis 12030 (1.25×10$^5$ cfu per animal), while 4 animals received the monoclonal antibody VH4E and 4 received normal rabbit serum (NRS). Animals were sacrificed on postoperative day 6 and the correct placement of the catheter was verified. The extent of native valve endocarditis was assessed and graded macroscopically, and subsequently valve vegetations were removed aseptically. The primary evaluation criterion was the bacterial count in the vegetation (cfu per vegetation). The mean and standard deviation was calculated for each group.

A pre-screen of a donor pool by opsonophagocytic assay (OPA) was used to identify the donor with the highest titers of opsonic antibodies against E. faecalis 12030. Healthy donor 2 showed the highest opsonic killing (82%) using 1:100 serum.

B-cells of donor 2 were immortalized using EBV, spread into tissue culture plates, and undiluted supernatants were tested by opsonophagocytic assay against E. faecalis 12030. The well with the highest opsonic killing was selected, and B-cells in the respective well were removed, cultured, and subsequently seeded into a new tissue-culture plate. After the 4th round, the content of the well with the highest titer was used to prepare mRNA and cDNA, and sequencing revealed the presence of one light chain variable domain, and 4 different heavy chain variable domains (see sequences as herein). After cloning of these heavy-light chain pairs into TCAE and transfection of these constructs into CHO cells, the recombinant monoclonal antibodies from the supernatants were used in an opsonophagocytic killing assay using 4 strains: E. faecalis 12030, E. faecium 1162 (CC17), S. aureus LAC (CA-MRSA) and S. aureus (patient isolate). Opsonic killing occurred in the presence of monoclonal antibodies in a dose-dependent manner, whereas the absence of the mAbs but presence of neutrophils and complement alone did not reduce viable counts.

An opsonophagocytic Inhibition Assay (OPIA) was performed with two of the mAbs (VH4E and VH8 showing the highest killing against the tested strains) to determine their target. Cell wall extracts of E. faecalis 12030 were treated with Proteinase K or NaIO4 to assess if a polysaccharide or a protein is the target of the mAbs. Opsonic activity of VH4E and VH8 was not inhibited when bacteria were treated with NaIO4 but was inhibited when bacteria were treated with proteinase, indicating that a polysaccharide is the target of the mAbs.

Passive immunotherapy with monoclonal antibodies VH4E and VH8 was studied in a mouse bacteremia model. In this model the inventors could demonstrate that VH4E and VH8 promote clearance of E. faecium E1162 and S. aureus LAC, whereas normal rabbit sera (NRS) did not protect from bacterial infection. The number of bacteria recovered from the liver and kidney of mice infected with both strains was significantly reduced compared to those not being treated with the mAbs. A lipoteichoic acid-specific serum (αLTA T5) was used as positive control because the inventors have shown previously that this serum is opsonic and protective against enterococcal strains.

Comparing monoclonal antibody VH4E with normal rabbit serum (NRS) in a rat endocarditis model, bacterial vegetations of VH4E-treated rats were significantly reduced (measured in cfu per milliliter and in milligram vegetation), compared to those not being treated with VH4E the day before bacterial challenge. The total amount of bacteria in vegetations was also lower in the group receiving the monoclonal antibody.

In a different animal model, bacteria were injected i.p. and mice received VH8 (4 µg/kg per mouse in 200 µl saline) 24 hours before bacterial challenge. At an inoculum of 2×108 per mouse, all mice receiving NRS died after 18 hours, while 3/8 (37.5%) of animals receiving the monoclonal antibody survived (FIG. 9).

Sequences as identified:

Light chain VL
(SEQ ID NO: 1)
LTMAGFPLLLTLLIHCTGSWAQSVLTQPPSVSAAPGQRVTISCSGSSSNL

GNNFASWYQQLPGAAPRLLIYDNDKRPSGIPDRFSGSKSGTSATLGITGL

QTGDEADYYCGTWDSSLTAYVFGSGTKVT

DNA-Light chain VL
(SEQ ID NO: 2)
CTCACCATGGCCGGCTTCCCTCTCCTCCTCACCCTTCTCATTCACTGCAC

AGGGTCCTGGGCCCAGTCTGTGTTGACGCAGCCGCCCTCAGTGTCTGCGG

CCCCAGGACAGAGGGTCACCATCTCCTGCTCTGGAAGCAGCTCCAACCTT

GGGAACAATTTTGCATCCTGGTACCAGCAACTCCCAGGAGCAGCCCCCCG

GCTCCTCATTTATGACAATGATAAGCGACCCTCAGGGATTCCTGACCGAT

TCTCTGGCTCCAAGTCTGGCACGTCAGCCACCCTGGGCATCACCGGGCTC

CAGACTGGGGACGAGGCCGATTATTACTGCGGAACATGGGATAGCAGCCT

GACTGCTTATGTCTTCGGAAGTGGGACCAAGGTCACCGT

Heavy chain VH2
(SEQ ID NO: 3)
GVGAELKKPGASVKVSCKASEYTFTTYDIIWVRQATGQGLEWMGWMNPNS

GDTGFAQKFQDRVTLTRNTSISTAYMELSSLRSEDTAVYYCSRAPRYDSW

SGYYSDFWGQGTLVTVSS

DNA-Heavy chain VH2
(SEQ ID NO: 4)
ATGGAGTTGGGGCTGAGCTGAAGAAGCCTGGGGCCTCAGTGAAGGTCTCC

TGCAAGGCTTCCGAATACACCTTCACCACTTATGATATCATCTGGGTGCG

GCAGGCCACTGGACAAGGGCTTGAGTGGATGGGATGGATGAATCCAAACA

```
GTGGAGACACAGGCTTTGCACAGAAATTCCAGGACAGAGTCACCTTGACC

AGAAACACGTCCATTAGCACAGCCTACATGGAGCTGAGCAGCCTGAGATC

TGAAGATACGGCCGTCTATTACTGTTCGAGAGCCCCTCGTTACGATTCTT

GGAGTGGTTATTACAGTGACTTCTGGGGCCAGGGAACCCTGGTCACCGTC

TCCTCA

Heavy chain VH3
                                        (SEQ ID NO: 5)
GAGAELKKPGASVKVSCKTSGYSLTNYGINWVRQAPGQGLEWMAWICGYN

GDTVFAQKFQGRVTMTTDTSTNTVYMDLRGLTSDDTAVYYCAKERRPFVA

PEGGMDAWGQGTTVTVSS

DNA-Heavy chain VH3
                                        (SEQ ID NO: 6)
ATGGAGCTGGGGCTGAGCTGAAGAAGCCTGGGGCCTCAGTGAAGGTCTCC

TGCAAGACTTCTGGTTACAGTTTAACCAACTATGGTATCAACTGGGTGCG

ACAGGCCCCGGACAAGGGCTTGAGTGGATGGCGTGGATCTGCGGTTACA

ATGGTGACACAGTCTTTGCACAGAAGTTCCAGGGCAGGGTCACCATGACC

ACAGACACATCCACGAACACAGTCTACATGGACCTGAGGGGCCTGACATC

TGACGACACGGCCGTGTATTACTGTGCGAAAGAGAGGCGGCCGTTTGTCG

CACCAGAAGGAGGTATGGACGCCTGGGGCCAAGGGACGACAGTCACCGTC

TCCTCA

Heavy chain VH4E
                                        (SEQ ID NO: 7)
GVGAELKKPGSSVKVSCKASGGSFASYAISWVRQAPGQGLEWMGAIIPVF

GTASYAQGFQGRVTISADKSTNVVNMELSSLFSEDTAVYFCARTYMWNTG

DWFFDLWGRGTLVTVSS

DNA-Heavy chain VH4E
                                        (SEQ ID NO: 8)
ATGGAGTTGGGGCTGAGCTGAAGAAGCCTGGGTCCTCGGTGAAGGTCTCC

TGCAAGGCCTCTGGAGGCTCGTTCGCCAGCTATGCTATCAGCTGGGTGCG

ACAGGCCCCTGGACAAGGGCTTGAGTGGATGGGAGCGATCATCCCTGTCT

TTGGTACAGCAAGCTACGCACAGGGGTTCCAAGGCAGAGTCACCATTTCC

GCGGACAAATCCACAAACGTAGTCAACATGGAGCTGAGCAGCCTGTTTTC

TGAGGACACGGCCGTCTATTTCTGTGCGAGGACTTACATGTGGAACACCG

GGGACTGGTTTTTCGATCTCTGGGGCCGTGGCACCCTGGTCACTGTCTCC

TCA

Heavy chain VH8
                                        (SEQ ID NO: 9)
GAGAELVKPGASVKLSCKASGYTFTSYWMHWVKQRPGRGLEWIGRIDPNS

GGTKYNEKFKNKGTLTVDTSSSTAYMHLSSLTSEDSAVYYCTRELPGTRY

FDVWGAGTTVTVSS

DNA-Heavy chain VH8
                                        (SEQ ID NO: 10)
ATGGAGCTGGGGCTGAGCTTGTGAAGCCTGGGGCTTCAGTAAAGCTGTCC

TGCAAGGCTTCTGGCTACACCTTCACCAGCTACTGGATGCACTGGGTGAA

GCAGAGGCCTGGACGAGGCCTCGAGTGGATTGGAAGGATTGATCCTAATA

GTGGTGGTACTAAGTACAATGAGAAGTTCAAGAACAAGGGCACACTGACT

GTAGACACATCCTCCAGCACAGCCTACATGCACCTCAGCAGCCTGACATC

TGAGGACTCTGCGGTCTATTACTGTACAAGAGAACTACCTGGGACCCGGT

ACTTCGATGTCTGGGGCGCAGGGACCACTGTCACCGTCTCCTCA
```

REFERENCES AS CITED

1. Kelly-Quintos, C., Cavacini, L. A., Posner, M. R., Goldmann, D. A. & Pier, G. B. Characterization of the opsonic and protective activity against *Staphylococcus aureus* of fully human monoclonal antibodies specific for the bacterial surface polysaccharide poly-N-acetylglucosamine. *Infect Immun* 74, 2742-2750 (2006).
2. Theilacker, C. et al. Glycolipids are involved in biofilm accumulation and prolonged bacteraemia in *Enterococcus faecalis*. *Mol Microbiol* 71, 1055-1069 (2009).
3. Hufnagel, M., Koch, S., Creti, R., Baldassarri, L. & Huebner, J. A putative sugar-binding transcriptional regulator in a novel gene locus in *Enterococcus faecalis* contributes to production of biofilm and prolonged bacteremia in mice. *J INFECT DIS* 189, 420-430 (2004).
4. Theilacker, C. et al. Protection against *Staphylococcus aureus* by antibody to the polyglycerolphosphate backbone of heterologous lipoteichoic acid. *J INFECT DIS* 205, 1076-1085 (2012).
5. Theilacker, C. et al. Serodiversity of Opsonic Antibodies against *Enterococcus faecalis*—Glycans of the Cell Wall Revisited. *PLoS ONE* 6, e17839 (2011).
6. Haller C, Berthold M, Wobser D, Kropec A, Lauriola M, et al. (2014) Cell-Wall Glycolipid Mutations and Their Effects on Virulence of *E. faecalis* in a Rat Model of Infective Endocarditis. PLoS ONE 9: e91863. doi: 10.1371/journal.pone.0091863.
7. Bao Y, Li Y, Jiang Q, Zhao L, Xue T, Hu B, Sun B. Methylthioadenosine/S-adenosylhomocysteine nucleosidase (Pfs) of *Staphylococcus aureus* is essential for the virulence independent of LuxS/AI-2 system. Int J Med Microbiol. 2013 May; 303(4):190-200. doi: 10.1016/j.ijmm.2013.03.004. Epub 2013 Mar. 29.
8. Tosato G, Cohen J I (2007) Generation of Epstein-Barr Virus (EBV)-immortalized B cell lines. Curr Protoc Immunol Chapter 7: Unit7.22. doi:10.1002/0471142735.im0722s76.

The invention claimed is:

1. A method for treating an infection caused by a Gram-positive bacterium comprising administering to a patient in need of such treatment or therapy a therapeutically effective amount of a pharmaceutical composition comprising an opsonic monoclonal antibody specific for Gram-positive bacteria, comprising a light chain and a heavy chain, wherein said light chain comprises a polypeptide comprising a light chain variable region of SEQ ID NO: 1, and wherein said heavy chain comprises a polypeptide comprising a heavy chain variable region selected from the group consisting of SEQ ID NOs: 3, 5, 7, and 9; and wherein the Gram-positive bacterium is *Staphylococcus aureus*.

2. The method according to claim 1, wherein the Gram-positive bacterium is antibiotic resistant.

3. The method, according to claim 1, wherein the light chain, the heavy chain, or both, are chimeric.

4. The method, according to claim 1, wherein the antibody comprises a heavy chain constant region, wherein said constant region comprises a human IgG, IgA, IgM, or IgD sequence.

5. The method, according to claim 1, wherein the antibody comprises a Fab, Fab', F(ab')2, Fv, SFv, or scFv.

6. The method, according to claim 1, wherein the antibody comprises a light chain constant region comprising a human kappa or lambda sequence.

* * * * *

UNITED STATES PATENT AND TRADEMARK OFFICE
CERTIFICATE OF CORRECTION

PATENT NO.          : 10,100,103 B2
APPLICATION NO.     : 15/108398
DATED               : October 16, 2018
INVENTOR(S)         : Johannes Hubner et al.

It is certified that error appears in the above-identified patent and that said Letters Patent is hereby corrected as shown below:

In the Specification

Column 13
Line 21, "5. Times. 106" should read --$5 \times 10^6$--.
Line 24, "1 .mu.1 volume" should read --1 µl volume--.
Line 26, "50 .mu.1 PCR" should read --50 µl PCR--.
Line 28, "1 .mu.1 cDNA" should read --1 µl cDNA--.

Signed and Sealed this
Second Day of July, 2019

Andrei Iancu
*Director of the United States Patent and Trademark Office*